United States Patent [19]
Keshaviah

[11] Patent Number: 5,507,723
[45] Date of Patent: Apr. 16, 1996

[54] METHOD AND SYSTEM FOR OPTIMIZING DIALYSIS CLEARANCE

[75] Inventor: Prakash R. Keshaviah, Plymouth, Minn.

[73] Assignee: Baxter International, Inc., Deerfield, Ill.

[21] Appl. No.: 248,025

[22] Filed: May 24, 1994

[51] Int. Cl.$^6$ .................................................. A61M 37/00
[52] U.S. Cl. .................................... 604/5; 604/65; 604/19; 210/647
[58] Field of Search ............................ 604/4, 5, 31, 65, 604/28, 29, 19; 210/646, 647, 321.65, 321.71

[56] References Cited

U.S. PATENT DOCUMENTS

| | | |
|---|---|---|
| 4,244,787 | 1/1981 | Klein et al. . |
| 4,990,258 | 2/1991 | Bjare et al. ............................ 210/647 |
| 4,995,268 | 2/1991 | Ash et al. ............................... 210/647 |
| 5,024,756 | 6/1991 | Steinby .................................. 210/647 |
| 5,091,094 | 2/1992 | Veech .................................... 210/647 |

(List continued on next page.)

FOREIGN PATENT DOCUMENTS

| | | |
|---|---|---|
| 0272414A2 | 6/1988 | European Pat. Off. . |
| 0532433A1 | 3/1993 | European Pat. Off. . |
| 2624384A1 | 12/1976 | Germany . |
| 2825134A1 | 12/1978 | Germany . |

OTHER PUBLICATIONS

Schneditz et al., *Cardiopulmonary Recirculation During Dialysis: Mathematical Analysis, Measurement and Effects on Computation of Urea Distribution Volume and Access Recirculation*, Evolving Dialysis: Advances in Technology, Beth Israel Medical Center, New York (1992).

Collins et al., *Recirculation and Effective Clearnaces*, Am. Soc. of Nephrology, 20th Annual Meeting, Washington, D.C. (1987).

Daniels et al., *Blood Flow Rate and Access Recirculation in Hemodialysis*, The International Journal of Artificial Organs, vol. 15, No. 8, pp. 470–474 (1992).

Schmidt et al., *Inaccurate Blood Flow Rate During Rapid Hemodialysis*, American Journal of Kidney Diseases, vol. XVII, No. 1, pp. 34–37 (1991).

Collins et al., *Fistula Dysfunction: Effect of Rapid Hemodialysis*, Kidney International, vol. 41, pp. 1292–1296 (1992).

*OPUS II Single Needle Dialysis*, The Medical Department, Gambro, Inc. (1981).

Sherman et al., *Rate–Related Recirculation: The Effect of Altering Blood Flow on Dialyzer Recirculation*, American, Journal of Kidney Diseases, vol. XVII, No. 2, pp. 170–173 (1991).

Baldasseroni et al., *Clinical Evaluation of the Magnitude of Blood Recirculation in the Single Needle Dialysis System*, J.AANT, vol. 1, No. 1, pp. 29–35 (1974).

Swamy et al., *Determination of Recirculation in a Single-–lumen Needle Hemodialysis System*, ASAIO Journal, vol. 3, pp. 29–32 (1980).

Hester et al., *An Non–invasive Determination of Recirculation in the Patient on Dialysis*, ASAIO Journal, pp. M190–M193 (1992).

Hester et al., *A New Technique for Determining Recirculation in the ESRD Patient*, Nephrology News & Issues, pp. 44–45 (Jun. 1993).

(List continued on next page.)

*Primary Examiner*—Corrine McDermott
*Assistant Examiner*—N. Kent Gring
*Attorney, Agent, or Firm*—Thomas S. Borecki; Charles R. Mattenson; Robert M. Barrett

[57] ABSTRACT

A system and method using same are provided for determining the optimum operating conditions of a dialysis process that yields the highest whole body dialysis clearance. The system varies a parameter that effects dialysis efficiency during part of a dialysis run. The system then measures a metabolite concentration in an outflow dialysate. The system develops a metabolite concentration profile as a function of the varied parameter. Based on these measurements, the system correlates the metabolite concentration measurements to determine the optimum parameter setting that yields the maximum metabolite concentration.

19 Claims, 4 Drawing Sheets

OTHER PUBLICATIONS

| | | | |
|---|---|---|---|
| 5,092,836 | 3/1992 | Polaschegg | 210/646 |
| 5,098,373 | 3/1992 | Polaschegg . | |
| 5,100,554 | 3/1992 | Polaschegg | 210/646 |
| 5,110,477 | 5/1992 | Howard et al. | 210/321.71 |
| 5,247,434 | 9/1993 | Peterson et al. | 210/646 |
| 5,308,315 | 5/1994 | Khuri et al. | 604/4 |
| 5,401,238 | 3/1995 | Pirazzoli . | |

METHOD AND SYSTEM FOR OPTIMIZING DIALYSIS CLEARANCE

BACKGROUND OF THE INVENTION

The present invention relates generally to hemodialysis machines. More specifically, the present invention relates to methods and systems for obtaining high whole body dialysis clearance during a dialysis process.

Using dialysis to support a patient whose renal function has decreased to the point where the kidneys no longer sufficiently function is well known. Two principal dialysis methods are utilized: hemodialysis; and peritoneal dialysis. The present application focuses on monitoring the effectiveness of a hemodialysis system.

In hemodialysis, the patient's blood is passed through an artificial kidney or dialyzer. The dialyzer purifies the blood by allowing diffusion of solutes from the blood across the dialyzer membrane into dialysate. Because it is an extracorporeal treatment that requires special machinery, certain factors must be considered when performing hemodialysis.

One of the most basic considerations in treating a patient with hemodialysis revolves around treatment adequacy. Quite simply, how long should a given patient be dialyzed on a given day. A number of medically adverse effects may result from an inadvertent failure to sufficiently dialyze the patient. At the present time, the average dialysis patient has a life expectancy of only about five years.

One reason these patients tend to have a short life expectancy is the deleterious effect of a chronic buildup of various toxins that either are not eliminated at all, i.e. do not pass through the hollow fiber membranes, or are not sufficiently reduced to nontoxic levels. The identity of many of these supposed toxins is not known, although those species known to be eliminated in urine, such as urea, creatinine, phosphate, hydrogen ions, etc. are associated with serious medical consequences when permitted to accumulate in excess of normal levels.

One measure of the adequacy of dialysis for the individual patient during a given treatment is calculated from the following equation:

$$KT/V \geq 1.0$$

Here K is the urea clearance of the dialysis process in milliliters (ml) of blood cleared of urea each minute. V is an expression of volume of distribution of urea which is approximately equal to the total body water volume. T is the treatment time. K/V is obtained from two blood samples, one taken prior to the start of dialysis and one taken at the end of dialysis. Upon incorporating K/V and T into the above equation, the degree of adequacy of the dialysis process can be determined.

In an effort to increase efficiency of hemodialysis, the industry continually makes further refinements to the hemodialysis process. The performance of a hemodialyzer (BUN clearance) can be affected by several factors related to the patient's vascular access such as: degree of access recirculation, cardiopulmonary recirculation, access flow, and the suction pressure developed by the hemodialysis delivery system blood pump as it pulls blood into the extracorporeal circuit. See Collins, D., et al., *Fistula dysfunction: Effect on rapid hemodialysis*, Kidney International, 41: 1292–1296 (1992); Daniel, I. D., G. M. Berlyne, and R. H. Barth, *Blood flow rate and access recirculation in hemodialysis*, The International Journal of Artificial Organs, 15(8): 470–474 (1992); Schneditz, D., et al. *Cardiopulmonary Recirculation During Dialysis: Mathematical Analysis, Measurement, and Effects on Computation of Urea Distribution Volume and Access Recirculation in Evolving Dialysis: Advances in Technology,* 1992, Beth Israel Medical Center, New York (1992); and Schmidt, D., et al., *Inaccurate Blood Flow Rate During Rapid Hemodialysis*, American Journal of Kidney Diseases, XVII(1): 34–37 (1991). Parameters that may be varied to achieve adequate dialysis include blood flow rate, dialysis solution flow rate, dialyzer competency and temperature.

Among other parameters, many in the industry have studied the effects of blood flow rate on the performance of a hemodialyzer. Generally, as blood flow increases, clearance increases. Raising the blood flow rate increases dialyzer clearance of small molecular weight solutes, and higher blood flow rates have been more and more widely used to improve dialysis efficiency. However, with conditions like access recirculation, increasing blood flow may actually decrease clearance. See Collins, A., et al., *Recirculation and effective clearances*, in Am. Soc. of Nephrology; 20th Annual Meeting, Washington, D.C. (1987).

The greater degree of recirculation occurring at higher blood flow rates may neutralize or reverse the increased clearance obtained with the higher blood flow rates. Recirculation of blood during dialysis occurs when insufficient blood flow through the A–V fistula exists in relation to the blood pump flow. This recirculation may be due to either venous stenosis or pump flow rates higher than access flow. Recirculation will reduce the clearance of solutes, resulting in inadequate dialysis in the short-term and potentially long-term detrimental effects on the health of the patient. Hester et al., *A New Technique for Determining Recirculation in the ESRD Patient*, Nephrology News and Issues, p. 44–45 (June 1993).

Access recirculation of blood flow is normally estimated from three simultaneous measurements of blood urea nitrogen (BUN). Blood samples are taken from the dialyzer inflow line, the dialyzer outflow line, and from a systemic sample. This method has accuracy problems for the true systemic blood sample because of the collection site, and because of the laboratory errors in the BUN measurement. The BUN technique for the determination of recirculation also has several disadvantages: removal of blood from anemic patients; additional exposure of health care workers to blood products; an added cost for the BUN determinations; and the lack of an instantaneous determination of recirculation. See Hester et al., supra.

In light of these problems, a need exists for a system that not only monitors the various factors effecting BUN clearance but also determines the optimum operating conditions to obtain the highest whole body clearance. No simple method currently exists that accounts for the various factors that effect BUN clearance, although repeated blood sampling before and after the dialyzer at different blood flow rates could conceivably yield the desired information. Therefore, providing a non-invasive, on-line monitoring system that determines the optimum parameter settings would be desirable.

SUMMARY OF THE INVENTION

The present invention provides a method and system for obtaining high whole body dialysis clearance in a dialysis system. The invention detects specific parameter settings of a hemodialysis delivery system at which no further increase in BUN clearance occurs, thereby determining the settings of specific parameters which yield the highest whole body clearance.

To this end, a method for obtaining the highest whole body dialysis clearance in a dialysis system is provided. The method initially comprises varying a parameter that affects dialysis efficiency during a part of a dialysis run. Then, the method includes measuring a metabolite concentration in an outflow dialysate. Next, the method comprises developing a metabolite concentration profile as a function of the varied parameter. Analyzing the metabolite concentration profile as a function of the varied parameter enables one to determine the optimal settings of the parameters that yield the maximum metabolite concentration in the dialysate.

In an embodiment, the metabolite is selected from urea, creatinine, phosphate, or uric acid.

In an embodiment, the parameter being varied is blood flow rate. The blood flow rate may be stepwise varied in specified increments (e.g. 50 ml/min).

In an embodiment, the method of the present invention further includes the step of storing the optimum parameter setting associated with the maximum metabolite concentration.

The present invention also provides a system for obtaining the highest whole body dialysis clearance in a dialysis process. The system includes means for varying a parameter that affects dialysis efficiency during part of a dialysis run. In addition, the system includes means for measuring a metabolite concentration in an outflow dialysate. The system further includes means for developing a metabolite concentration profile as a function of the varied parameter. Still further, the system includes means for correlating the metabolite concentration measurements to determine the optimum parameter settings that yield a maximum metabolite concentration.

In an embodiment, the metabolite being measured is selected from urea, creatinine, phosphate, or uric acid.

In an embodiment, the parameter being varied is blood flow rate. The blood flow rate may be varied in specified increments (e.g. 50 ml/min).

In an embodiment, the system of the present invention further includes means for storing the optimum parameter setting associated with the maximum metabolite concentration.

An advantage of the present invention is that it provides an on-line method for determining the optimum blood flow to obtain the highest clearance in a dialysate.

Additionally, an advantage of the present invention is that no blood samples are required to find the blood flow associated with the highest clearance.

Another advantage of the present invention is that the sampled data is rapidly analyzed and does not have to be sent to a laboratory for analysis.

Still further, an advantage of the present invention is that it effectively decreases nursing time.

Yet another advantage of the present invention is that it eliminates the need for sterile disposables.

Another advantage of the present invention is that it addresses the concerns associated with recirculation without the need to measure recirculation per se.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to the monitoring of hemodialysis systems. In particular, the present invention provides a system and method for obtaining the highest whole body dialysis clearance in a dialysis system. To this end, the present invention determines optimal parameter settings in a dialysis system that yield the highest whole body dialysis clearance. In a preferred embodiment, the present invention determines the optimal blood pump setting to yield the highest dialysis clearance, thereby eliminating the need to find the amount of recirculation for blood pump adjustment.

Figure 1:
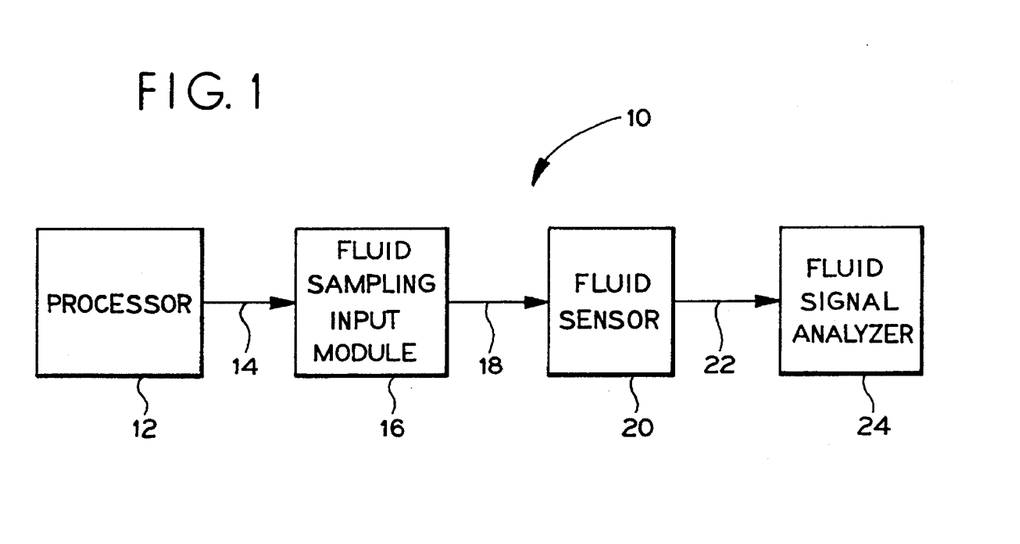
FIG. 1 is a block diagram of one embodiment of the hemodialysis monitoring system of the present invention.

Referring now to FIG. 1, one embodiment of a hemodialysis monitoring system of the present invention is designated generally by the reference numeral 10. The monitor 10 includes a processor 12. The processor 12 stepwise varies the selected parameter in defined increments. The processor 12 is connected to an input module 16 via a line 14. In the preferred embodiment, the module 16 can be a urea sensor or an appropriate sensor for sensing a different molecule or constituent to be cleared. The module 16 couples the dialysate sample volume to a sensor 20 via a line 18. The sensor 20 generates a signal which is proportional to the monitored constituent concentration and couples that signal to a constituent signal analyzer 24 via a line 22.

The processor 12 can be any suitable processor that will stepwise vary a selected parameter in defined increments. In an embodiment, the parameter to be varied is the blood flow rate. The processor 12 may, for example, stepwise increase the blood flow rate in 50 ml/min increments.

The module 16 can be any type of sampling device which is coupled, preferably permanently, to the dialysate effluent line (not illustrated). A preferred input module 16 is disclosed and described in U.S. patent application Ser. No. 07/960,088 filed Oct. 13, 1992, entitled FLUID SAMPLING MODULE, which is incorporated herein by reference. The urea sensor 20 can be a sensor as described in U.S. Pat. No. 4,686,479, entitled APPARATUS AND CONTROL KIT FOR ANALYZING BLOOD SAMPLE VALUES INCLUDING HEMATOCRIT, which also is incorporated herein by reference. The fluid signal analyzer 24 can be a signal analyzer as described in U.S. patent application Ser. No. 07/959,922, filed Oct. 13, 1992, entitled HEMODIALYSIS MONITORING SYSTEM FOR HEMODIALYSIS MACHINES, which is incorporated herein by reference.

The liquid sample is contacted with a urea sensor that includes a urease layer associated with an electrode adapted to generate output in response to ammonium ions. The urease layer converts a portion of the urea in the sample to ammonium ions, and the ions contact the electrode to generate output related to the urea concentration in the sample.

The sensor 20 is described herein for example purposes, as a urea sensor. There are other approaches to urea sensing and any urea sensor that can measure urea concentration in the effluent dialysate line can be utilized for this purpose. The invention, therefore, is not specific to a particular type of urea sensor. Urea, however, is just one of a number of identifiable constituents generally related to uremia in a patient's blood, which can be utilized as a marker or measure of the effectiveness of the hemodialysis treatment, i.e. the removal of toxins. Such other constituents are, for example, creatinine, uric acid, phosphate, calcium, sodium potassium, glucose, and beta 2 microglobulin. Other types of sensors also can be utilized in the hemodialysis monitoring system of the present invention, which sense the required fluid constituent(s) directly or indirectly.

There are also other approaches to the flow configuration of the urea sensor. The most direct configuration is location of the urea sensor in the effluent dialysate stream. Another direct configuration is taking the sample volume from the fluid stream and flowing the sample volume past the sensor. Other configurations could include:

1. Locating the sensor in the fresh inflow dialysate stream with effluent dialysate being pumped in, upstream of the sensor, in a flow injection mode.

2. Pumping inflow and outflow streams in the desired proportions for dilution past the urea sensor.

3. A flow injection scheme where a carrier buffer stream is pumped past the urea sensor with injection of effluent dialysate into this buffer stream.

Figure 2:
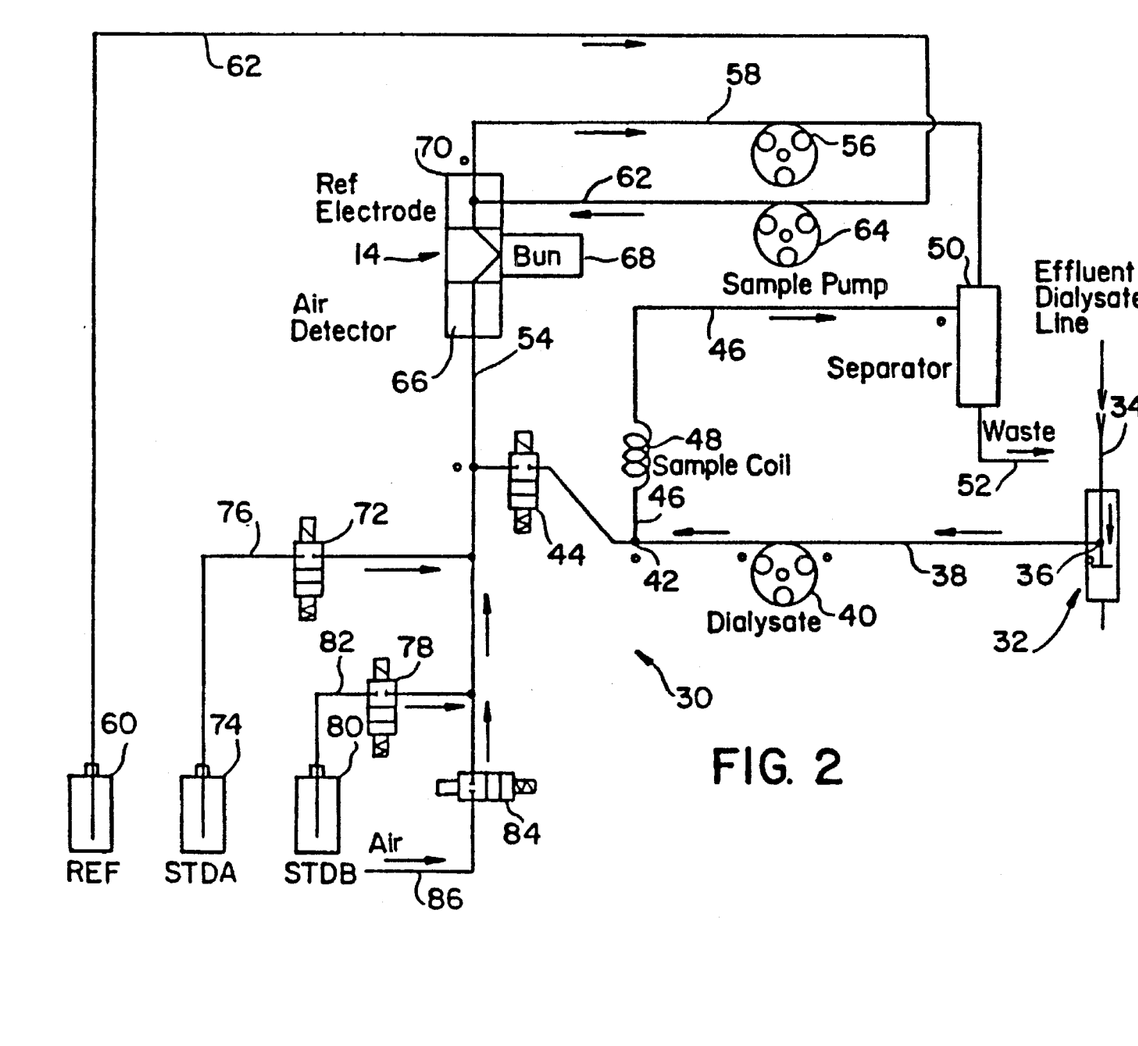
FIG. 2 is a schematic diagram of one embodiment of a portion of the hemodialysis monitoring system of FIG. 1.

One urea input/sensor module embodiment of the urea input module 16 and the urea sensor 20 of the hemodialysis monitoring system 10 of the present invention is designated generally by the reference numeral 30 in FIG. 2. The module 30 includes a sample port 32, which preferably forms a part of a discharge or dialysate effluent line 34. The module 30 taps into the dialysate effluent line 34 via a junction 36 coupled to a sampling line 38.

The module 30 samples the dialysate effluent by activating a self occluding peristaltic or roller pump 40. The line 38 is coupled to a junction 42 and to a normally closed valve 44. The junction 42 also is coupled to a line 46, which includes a storage coil 48. The storage coil 48 is first filled with the dialysate effluent, with the excess dialysate effluent continuing through the line 46 to a separator 50. The separator 50 includes an air gap, which prevents a backup of the dialysate effluent and also prevents an electrical short through the line 52.

Once the storage coil 48 is filled, the pump 40 is stopped, which closes the line 38 from the junction 36. The valve 44 then is opened allowing the sample dialysate to flow through the valve into a line 54 and then to and past the urea sensor 20. The sample dialysate is caused to flow by a sample pump 56, which is coupled between the urea sensor 20 and the discharge separator 50 by a line 58.

For each measurement, sample dialysate preferably is input to the urea sensor 20 and flushed through the separator 50 several times to ensure a good sample value. At the same time the sample dialysate is pumped through the urea sensor 20, a reference fluid from a source 60 also is pumped into the urea sensor 20 via a line 62 and a second pump 64. The second pump 64 preferably can be a second roller head on the sample pump 56, but could also be a second pump coupled to operate at the same time as the sample pump 56.

As shown in more detail in U.S. Pat. No. 4,686,479, the urea sensor 20 includes an air detector 66 to determine if the sample dialysate is present in the urea sensor 20. The sensor 20 employs an electrode 68 with a membrane (not illustrated) which is specific to ammonium. The electrode 68 senses dialysate urea nitrogen (DUN) which is compared to a reference electrode 70. The signal generated by the sensor 20 then is coupled to the signal analyzer 24.

At the beginning of the hemodialysis treatment with a patient and periodically as desired, both a low reference standard and a high reference standard are run on the module 30 to calibrate the module 30. To calibrate the module 30 with the low standard, the valve 44 remains closed and a valve 72 is opened to allow the second pump 64 to draw in the low standard fluid from a source 74 via a line 76. The urea sensor 14 measures the low standard, which is compared to an expected range of values to ensure that the urea sensor 20 is calibrated correctly. The low standard also can be utilized to test the integrity of the system during treatment.

A similar operation is performed with a high reference standard. To run a high standard test, all the valves are closed, except for a high standard valve 78. The open valve 78 allows the second pump 64 to draw a high standard fluid from a source 80 via a line 82. The high standard fluid is measured in the urea sensor 20 and compared to an expected range of values to ensure that the urea sensor also is operating correctly at the high standard range.

At the end of the low standard cycle testing, the module 30 closes the valves 44, 72 and 78 and opens an air valve 84 for a period of time, which allows the sample pump 64 to draw air into a line 86 through the valve 84, the urea sensor 20 and the discharge line 52. This air segment between each fluid segment helps ensure that the urea sensor 20 and the lines 54 and 58 are clean and empty of any substantial amount of residual fluid.

Figure 3:
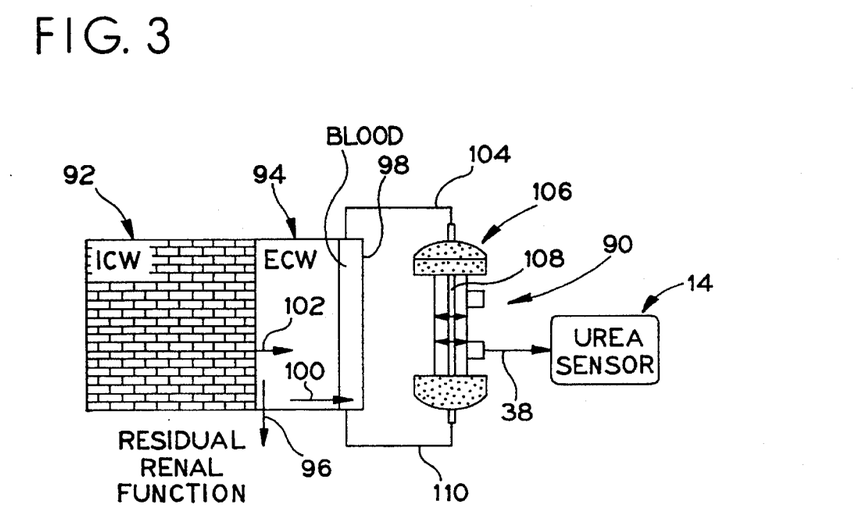
FIG. 3 is a partial block and partial schematic diagram of the fluid functions of a portion of the hemodialysis monitoring system of FIG. 1.

Referring now to FIG. 3, a schematic embodiment of one input/sensor/analyzer module of the monitoring system 10 of the present invention is designated generally by the reference character 90. The system 90 is depicted diagrammatically as including an intracellular space (ICW) 92 and an extracellular space (ECW) 94, which spaces are representative of the body pools in a hemodialysis patient. The hemodialysis kinetic parameters in the system 90 are calculated from the spent dialysate of a patient undergoing a typical dialysis treatment. The urea is generated in the liver, which is illustrated as being a portion of the ECW 94.

Some of the urea may be removed by the patient's kidneys, if there is a residual renal function, as indicated by an arrow 96. The majority of the urea, however, is removed by the hemodialysis treatment after first contacting the blood 98 in the ECW 94, as indicated by an arrow 100. Urea also enters the ECW 94 from the ICW 92, as indicated by an arrow 102.

The blood is removed during the hemodialysis treatment by flowing through a line 104 into a dialysis cartridge 106. The dialysis cartridge 106 diagrammatically includes a dialyzer membrane 108 across which urea diffuses into the dialysate. A sample volume of the dialysis effluent is removed through the line 38 and then is sensed by the urea sensor 14, as above described. The blood returns to the patient via a line 110.

Figure 4:
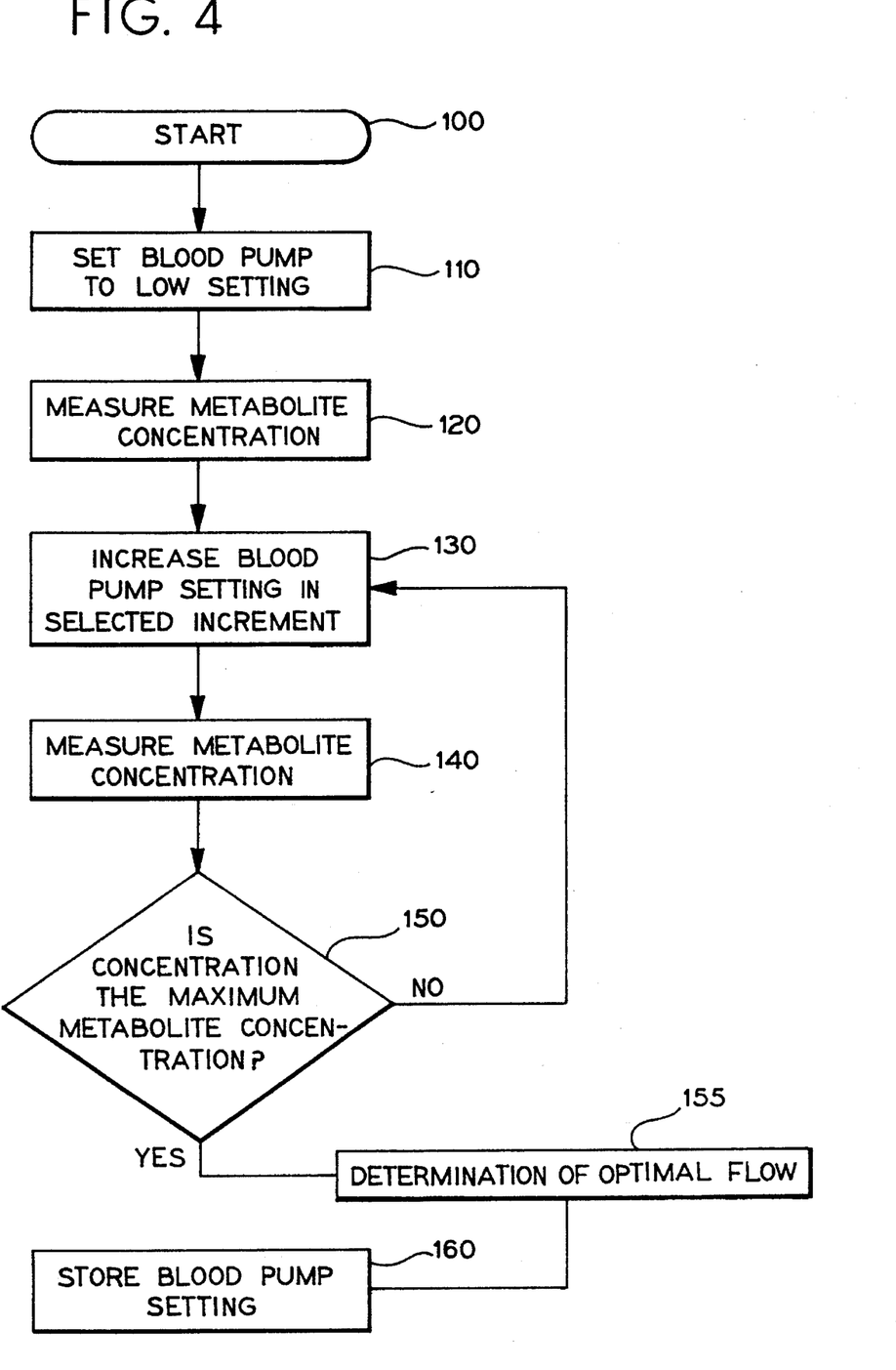
FIG. 4 illustrates a flowchart for operation of the present invention to obtain the highest whole body dialysis clearance in a dialysis system.

In use, the system 10 may function with reference to the flowchart illustrated in FIG. 4. For illustrative purposes only, the flowchart details the varying of blood flow rate to determine the optimal blood flow rate that will yield the highest whole body clearance. Naturally, those skilled in the art will appreciate that the same methodology of the present invention may also be utilized to optimize other parameters of a dialysis system. Such other parameters that effect dialysis efficiency are, for example, dialysis solution flow rate and temperature.

Referring now to FIG. 4, the system 10 may first be started at 100. The system 10 initially sets the blood pump to a low setting (at step 110) and then measures the metabolite concentration (at step 120). In an embodiment, the metabolite is urea. As stated above, optimal settings for parameters other than blood flow rate may be analyzed pursuant to the present invention. The initial setting (step 110), naturally, depends on the parameter being analyzed.

After measuring the metabolite concentration, the system 10 incrementally increases or decreases the blood pump setting at step 130. In an embodiment, the blood pump setting is increased in specified (e.g. 50 ml/min) increments. At step 120, the metabolite concentration is then measured.

At step 150, the system 10 determines whether the measured concentration of step 140 is the maximum metabolite concentration. This is done by comparing the current concentration with the previous concentration. If the current concentration is lower than the previous concentration by a certain amount (e.g. 1.0 mg/dl) then the previous concentration is the maximum concentration. If the measured concentration of step 140 is not the maximum concentration, the system 10 again increases (step 130) the blood pump setting by the specified increment (e.g. 50 ml/min). Then, the metabolite is again measured and compared with the previous measurement until the maximum concentration is reached. Likewise, blood flow can be set at an initial maximum; the metabolite concentration can be determined and then the blood pump setting can be decreased by a specified decrement, repeating the metabolite measurement until the maximum concentration is obtained.

When the maximum concentration has been obtained, the flow associated with the maximum metabolite concentration is determined (step 155). There are several ways to make this determination. For example, the maximum flow may simply be the blood pump setting that yields the maximum concentration. In another embodiment, a nonlinear curve may be fit to the concentration-flow data (e.g. a 2nd order parabola) by a least squares technique and the derivative of the curve taken. The maximum flow is then that flow at the point where the derivative of the concentration-flow curve is zero. This approach avoids problems introduced by the absence of continuous data and makes better use of the finite number of samples.

Figure 5:
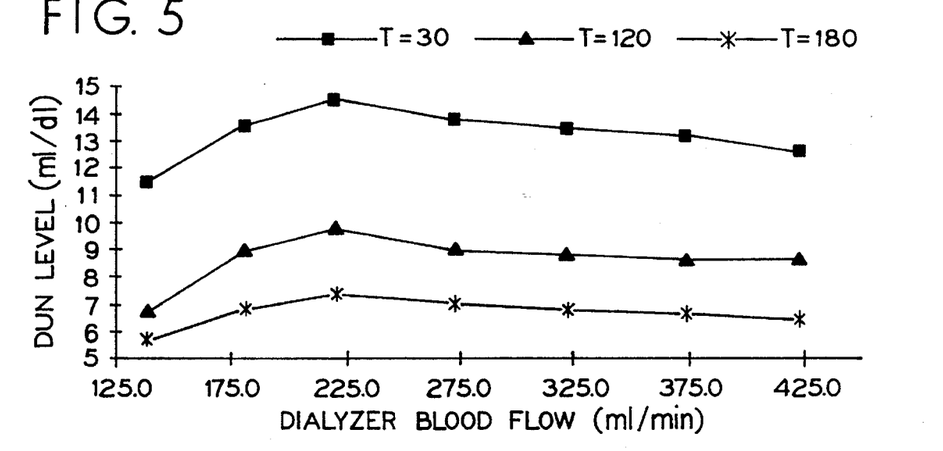
FIG. 5 illustrates the dialysate DUN level as a function of dialyzer blood flow and elapsed time in minutes since the initiation of dialysis in a simulated access (two needles placed in a latex rubber tube) whose flow rate is fixed at 200 ml/min. The DUN peaks closest to the access flow rate.
Figure 6:
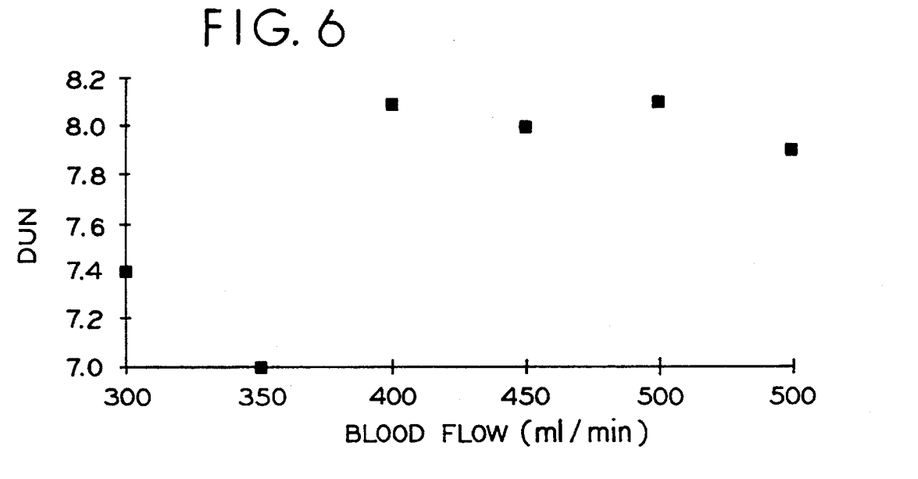
FIG. 6 illustrates the DUN level as a function of dialyzer blood flow for an actual patient at the beginning of a dialysis run. The optimal blood flow would be 400 ml/min.

FIG. 5 shows the result of this process in a simulated access which was prepared by placing two 15 gauge needles through the wall of a latex tube in which urea containing fluid was circulated at 200 ml/min into and out of a 40 liter tank through a dialyzer. Each curve which was generated at a different time in the dialysis process has a similar shape with the peak DUN level at around 200 ml/min which matches the access flow. FIG. 6 shows a similar effect in an actual patient where the maximum flow rate appears to be around 400 ml/min.

Figure 7:
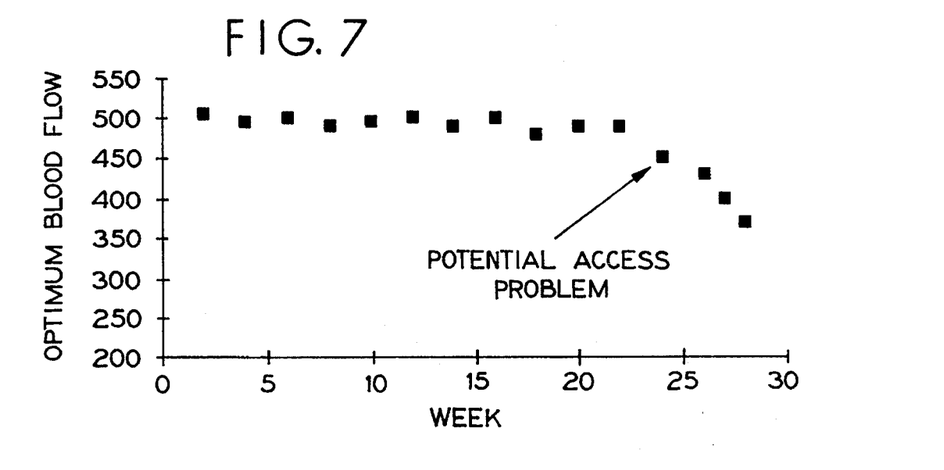
FIG. 7 illustrates how serial changes in optimal blood flow could potentially be used to assess the need for access revision.

Each of these optimum flow rates is stored by the device. When many such flow rates are obtained for different runs on the same patient, they can be compared as shown in FIG. 7. (Data in this figure is simulated.) When the optimal flow rate substantially decreases from the initial baseline (about 500 ml/min in the example), this indicates the need to investigate the revision of the access since there may be ingrowth of tissue at one of the anastomoses.

Running the system 10 at the optimum blood flow rate in turn yields the highest BUN clearance. The efficiency of urea removal (BUN clearance) by a hemodialyzer is a function of the incoming blood concentration, blood and dialysate flow rates, and mass transfer-area coefficient of the dialyzer. BUN clearance (K) can be quantified using the following calculation: effluent dialysate flow rate (QDo) multiplied by effluent dialysate urea concentration (CDo) divided by incoming plasma water urea concentration (CBi). In equation format then, $$K = CDo * QDo/CBi$$

At a constant QDo and CBi, CDo is dependent on K, which in turn is dependent on blood flow.

If the blood flow rate setting on the hemodialysis delivery system is increased in a stepwise fashion and rapid measurements of CDo at each setting are made, the achievement of maximum BUN clearance is approximately the setting at which CDo reaches a maximum. Since the BUN concentration of the blood in the patient's body is assumed to be constant, measurements of the effluent dialysate urea concentration must be made rapidly. Alternatively, the measurements should be made at a point in the dialysis process where the rate of change is relatively slow (i.e. toward the end of the dialysis). The present invention effectively conducts this procedure and as a result determines the optimum settings to achieve maximum BUN clearance.

The system 10 of the present invention effectively addresses the reasons recirculation is generally measured without actually measuring recirculation. Namely, the present invention addresses the need to: (1) quantitate the decrease in dialysis efficiency at the patient's standard blood pump setting revising the setting upward if the recirculation is low or downward if the recirculation is high, and (2) determine the need for a possible access revision if recirculation increases over time. Obtaining the optimal blood pump setting, pursuant to the present invention, eliminates the need to directly evaluate the amount of recirculation for purposes of blood pump adjustment.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for obtaining the highest whole body dialysis clearance in a dialysis system comprising the steps of:

varying a parameter that effects dialysis efficiency during part of a dialysis run;

measuring a metabolite concentration in an outflow dialysate;

developing a metabolite concentration profile as a function of the varied parameter from the metabolite concentration measurements; and correlating the metabolite concentration measurements to determine an optimum parameter setting that yields a maximum metabolite concentration.

2. The method of claim 1 wherein the parameter is blood flow rate.

3. The method of claim 2 further comprising stepwise increasing the blood flow rate in specified increments.

4. The method of claim 2 further comprising stepwise decreasing the blood flow rate in specified decrements.

5. The method of claim 2 further comprising the step of storing an optimum blood flow rate associated with the maximum metabolite concentration.

6. The method of claim 1 wherein the metabolite is selected from the group consisting of: urea, creatinine, phosphate, and uric acid.

7. The method of claim 1 further comprising measuring the metabolite concentration each time the parameter is varied.

8. A method for determining the optimum blood pump setting of a dialysis system to obtain the highest whole body dialysis clearance comprising the steps of:

varying a blood flow rate during a dialysis run;

measuring a metabolite concentration in an outflow dialysate;

developing a metabolite concentration profile as a function of the blood flow rate; and correlating the metabolite concentration measurements to determine an optimum blood flow rate setting that yields a maximum metabolite concentration.

9. The method of claim 8 wherein the metabolite is selected from the group consisting of: urea, creatinine, phosphate, and uric acid.

10. The method of claim 8 further comprising stepwise increasing the blood flow rate in specified increments.

11. The method of claim 8 further comprising stepwise decreasing the blood flow rate in specified decrements.

12. The method of claim 8 further comprising measuring the metabolite concentration each time the blood flow is varied.

13. The method of claim 8 further comprising the step of storing an optimum blood flow rate associated with the maximum metabolite concentration.

14. A system for obtaining the highest whole body dialysis clearance in a dialysis system comprising:

means for varying a parameter that effects dialysis efficiency during part of a dialysis run;

means for measuring a metabolite concentration in an outflow dialysate;

means for developing a metabolite concentration profile as a function of the varied parameter; and means for correlating the metabolite concentration measurements to determine an optimum parameter setting that yields a maximum metabolite concentration.

15. The system of claim 14 wherein the parameter is blood flow rate.

16. The system of claim 15 further comprising means for increasing the blood flow rate in specified increments.

17. The system of claim 15 further comprising means for decreasing the blood flow rate in specified decrements.

18. The system of claim 14 wherein the metabolite is selected from the group consisting of: urea, creatinine, phosphate, and uric acid.

19. The system of claim 14 further comprising means for storing an optimum parameter setting associated with the maximum metabolite concentration.

* * * * *